(12) United States Patent
Rodríguez et al.

(10) Patent No.: US 10,597,430 B2
(45) Date of Patent: Mar. 24, 2020

(54) CHIMERIC GENE FOR HETEROLOGOUS EXPRESSION WHICH ENCODES FOR PEPTIDES WITH ANTIMICROBIAL ACTIVITY

(71) Applicant: Instituto de Investigaciones Agropecuarias, Santiago (CL)

(72) Inventors: Eduardo Andrés Tapia Rodríguez, Santiago (CL); Christian Fernando Montes Serey, Santiago (CL); Humberto Godofredo Prieto Encalada, Santiago (CL); Fabiola Alejandra Altamira Passalacqua, Santiago (CL); Gloria María Arenas Díaz, Santiago (CL)

(73) Assignee: Instituto de Investigaciones Agropecuarias, Santiago (CL)

( * ) Notice: Subject to any disclaimer, the term of this patent is extended or adjusted under 35 U.S.C. 154(b) by 0 days.

(21) Appl. No.: 15/164,549

(22) Filed: May 25, 2016

(65) Prior Publication Data

US 2016/0257724 A1    Sep. 8, 2016

Related U.S. Application Data

(63) Continuation-in-part of application No. 13/784,243, filed on Mar. 4, 2013, now abandoned.

(30) Foreign Application Priority Data

Mar. 4, 2013  (CL) .................................. 13/784,243

(51) Int. Cl.
C07K 14/435 (2006.01)

(52) U.S. Cl.
CPC .............................. C07K 14/43504 (2013.01)

(58) Field of Classification Search
None
See application file for complete search history.

(56) References Cited

U.S. PATENT DOCUMENTS

| 6,699,689 B1 * | 3/2004 | Kim | .................... | C07K 14/4723 435/183 |
| 7,935,501 B2 * | 5/2011 | Jensen | ............... | C07K 14/4723 424/442 |

OTHER PUBLICATIONS

Arenas et al. Peptides (2009),pp. 1-7.*
Tapia et al. Peptide (2011),32:1901-1916.*
Benjamin Zeitler (Dissertation (2010): Molecular farming: production of Antimicrobial Peptides in Different Nicotiana species).*
Gloria Arenas et al., "A novel antifungal peptide designed from the primary structure of a natural antimicrobial peptide purified from Argopecten purpuratus hemocytes", Peptides, 2009 doi: 10:1016, pp. 1-7.
Marion M . Bradford, "A Rapid and Sensitive Method for the Quantitation of Microgram Quantities of Protein Utilizing the Principle of Protein-Dye Binding", Analytical Biochemistry, vol. 72, 1976, pp. 248-254.
Willem F. Broekaert et al., "Antimicrobial Peptides from Plants", Critical Reviews in Plant Sciences, vol. 16, No. 3, 1997, p. 297-323.
Philippe Bulet et al. "Anti-microbial peptides: from invertegrates to vertebrates", Immunological Reviews, vol. 198, 2004, pp. 169-184.
Markus Fuhrmann et al., "Monitoring dynamic expression of nuclear genes in "*Chlamydomonas reinhardtii*" by using a synthetic luciferase reporter gene", Plant Molecular Biology, vol. 55, 2004, pp. 869-881.
Al-Guo Gao et al., "Fungal pathogen protection in potato by expression of a plant defensin peptide", Nature Biotechnology, vol. 18, Dec. 2000, pp. 1307-1310.
Havard Jenssen et al., "Peptide Antimicrobial Agents", Clinical Microbiology Reviews, vol. 19, No. 3, Jul. 2006, pp. 491-511.
Robert I. Lehrer et al., "Defensins of vertebrate animals", Current Opinion in Immunology, vol. 14, 2002, pp. 96-102.
Sergio H. Marshall et al., "Antimicrobial Peptides: A Natural Alternative to Chemical Antibiotics and a Potential for Applied Biotechnology", Electronic Journal of Biotechnology, vol. 6, No. 2, Aug. 2003, p. 271-284.
Tsuyoshi Nakagawa et al., "Development of Series of Gateway Binary Vectors, pGWBs, for Realizing Efficient Construction of Fusion Genes for Plant Transformation", Journal of Bioscience and Bioengineering, vol. 104, No. 1, 2007, p. 34-41.
Tsuyoshi Nakagawa et al., "Gateway Vectors for Plant Transformation", Plant Biotechnology, vol. 26, 2009, p. 275-284.
Imogen Sparkes et al., "Rapid, Transient Expression of Fluorescent Fusion Proteins in Tobacco Plants and generation of Stably Transformed Plants", Nature Protocols, vol. 1, No. 4, 2006, p. 2019-2025.
J. Andy Tincu et al., "Antimicrobial Peptides from Marine Invertebrates", Antimicrobial Agents and Chemotherapy, vol. 48, No. 10, Oct. 2004, p. 3645-3654.
Michael R. Yeaman et al., "Mechanisms of Antimicrobial Peptide Action and Resistance", Pharmacological Reviews, vol. 55, No. 1, 2003, p. 27-55.
Michael Zasloff, "Antimicrobial Peptides of Multicellular Organisms", Nature, vol. 415, Jan. 24, 2002, p. 389-395.

* cited by examiner

*Primary Examiner* — Medina A Ibrahim
(74) *Attorney, Agent, or Firm* — Greer, Burns & Crain, Ltd.

(57) ABSTRACT

The present invention relates to a chimeric nucleotide sequence encoding peptides with antimicrobial activity, to be expressed on plants as bioreactors, plant cell or transformed plant material and *E. coli*, where plants and bacteria were used for scale-up production of antimicrobial peptide and that produces the peptide sequence derived from nucleotide sequence SEQ ID No. 1, SEQ ID No. 6 and SEQ ID No. 12. It includes a method for obtaining the amino acids sequence SEQ ID No. 9 derived from a chimeric nucleotide sequence which encodes to antimicrobial peptides, wherein said amino acids sequence is derived from the synthetic DNA sequence SEQ ID No. 1, obtained from a back-translation of the amino acid sequence of the peptide Ap-S of *Argopecten purpuratus* scallop.

5 Claims, 6 Drawing Sheets

Specification includes a Sequence Listing.

CHIMERIC GENE FOR HETEROLOGOUS EXPRESSION WHICH ENCODES FOR PEPTIDES WITH ANTIMICROBIAL ACTIVITY

CROSS-REFERENCE TO RELATED APPLICATIONS

This application is a continuation-in-part of U.S. patent application Ser. No. 13/784,243 filed on Mar. 4, 2013, the disclosure of which is incorporated herein by reference in its entirety.

FIELD OF THE INVENTION

This invention relates to a chimeric nucleotide sequence encoding peptides with antimicrobial activity

BACKGROUND OF THE INVENTION

Antimicrobial peptides (AMP) are found in nature and have been isolated from several organisms including animals and plants. In recent years these molecules have shown an important anti-pathogenic capacity over Gram positive, Gram negative and fungi. AMPs are usually composed of 12-50 cationic and amphipathic amino acids (Broekaert et al., 1997; Zasloff de 2002, Marshall and Arenas, 2003). The natural AMP are divided into groups characterized by peptides formed by β sheets, α-helices, extended structures and helix loop or loop structures, and of them, the first two are the most abundant (Dathe et al., 1999; Gao et al., 2000; Lehrer and Ganz, 2002; Bulet et al., 2004). The interaction between AMPs and their target cells is markedly influenced by factors such as the type and scope of their structure, cationic property, hydrophobicity, amphipathic property and amino acid sequence (Yeaman and Yount, 2003; Jenssen et al., 2006; Soltani et al., 2007). Over 2300 peptides have been described and information on their structures, properties and mechanisms of action can be found in databases such as APD, ANTIMIC and AMPer.

In recent times the AMP have grabbed the attention as new substitutes of conventional pesticides and antibiotics, as pathogens do not develop resistance to them because of their mechanism of action (Yeaman and Yount, 2003). However, the use of peptides as alternative drugs has encountered some difficulties, among these we highlight the low recovery obtained after extraction from the tissue of origin. Therefore, obtaining by chemical synthesis or expression the protein in a recombinant microorganism strategy has become necessary for further studies. Interestingly, synthetic analogs or AMP derivatives have been successfully developed on the basis of natural peptides, generating significant improvements in their antimicrobial activity.

Most marine invertebrates are fixed to a substrate. Due to this sedentary condition, these organisms have evolved effective antimicrobials mechanisms among which are the AMPs (Tincu and Taylor, 2004). AMPs have been purified mainly from mollusks like mussels, oysters, scallops and gastropods. Arenas et al. (2009) obtained and characterized a form of an AMP native of chilean oyster (*A. purpuratus hemocytes*) by means of chemical synthesis. This new molecule (Ap-S) showed the presence of a secondary structure polyproline type, with a reduced amount of β sheet due to differential distribution of hydrophobic and hydrophilic residues in two well defined zones in N- and C-terminus, compared to the native peptide (Ap). Ap-S showed no cytotoxic effect in fish cell line CHSE-214. These findings in the Ap-S molecule newly generated, make their evaluation for various biotechnological applications be a reasonable option, including the exogenous application to control important plant pathogens. In this regard, the scaled up synthesis of this peptide becomes important for possible industrial application.

SUMMARY OF THE INVENTION

This application describes the design and use of a chimeric gene encoding for the recombinant version of Ap-S (rAp-S) which is expressed in *E. coli* strain BL21 and *Nicotania tabacum*. The results of the evaluation of rAp-S against plant pathogens, exemplified in fungi *Trichoderma harzianum*, *Botrytis cinerea*, *Fusarium oxysporum* and *Alternaria* sp., as well as Gram positive bacteria *Clavibacter michiganensis* and Gram negative *Xanthomona campestris* indicated that the production at a middle-high scale of this peptide leads to the production of a biologically active AMP that can be successfully used with this type of phytopathogens.

An objective of the invention es to provide a nucleotide sequence encoding recombinant antimicrobial peptides of Ap-S with antifungal and bactericidal activity, and then provide a method for obtaining the amino acids sequence SEQ ID No. 9 derived from a chimeric nucleotide sequence which encodes to antimicrobial peptides, wherein said amino acids sequence is derived from the synthetic DNA sequence SEQ ID No. 1, obtained from a back-translation of the amino acid sequence of the peptide Ap-S of *Argopecten purpuratus* scallop.

DETAILED DESCRIPTION OF THE INVENTION

The present invention relates to the generation of a nucleotide sequence encoding for antimicrobial peptides.

The technical basis of the present invention is that, despite knowing the existence of peptides with antimicrobial activity for eukaryotic organisms such as shellfish, it is only possible to extract only a small amount of peptide from animal tissue; this forces us to look for alternative techniques of production, such as chemical synthesis, which despite allowing generate greater amounts of peptide, it is limited by its high cost. An alternative is the use of genetic engineering and the use of heterologous expression systems to produce appropriate amounts in recombinant organisms. The advantage of this alternative technique is that through it greater amounts of peptide can be produced that will allow a more complete characterization and the actual evaluation of their biotechnological potential. However, this developmental pathway has some difficulties presented by the fact that there are many possible combinations of nucleotides derived from uses of codons, to correctly define a final active peptide.

The invention provides a synthetic gene for the AMP, Ap-S, which allows obtaining large amounts and raise its projection to the use in various industrial problems, such as agriculture.

In order to obtain adequate amounts of rAp-S peptide, we proceeded to design the synthetic gene and establishing a cloning strategy of synthetic sequence in an expression vector, in order to provide synthetic peptides that are suitable for controlling fungi and bacteria, and also provide synthetic peptides in quantities sufficient to be used as antipathogenic agents for activities such as agriculture, veterinary and/or medicine.

EXAMPLES

Example 1

Figure 1:
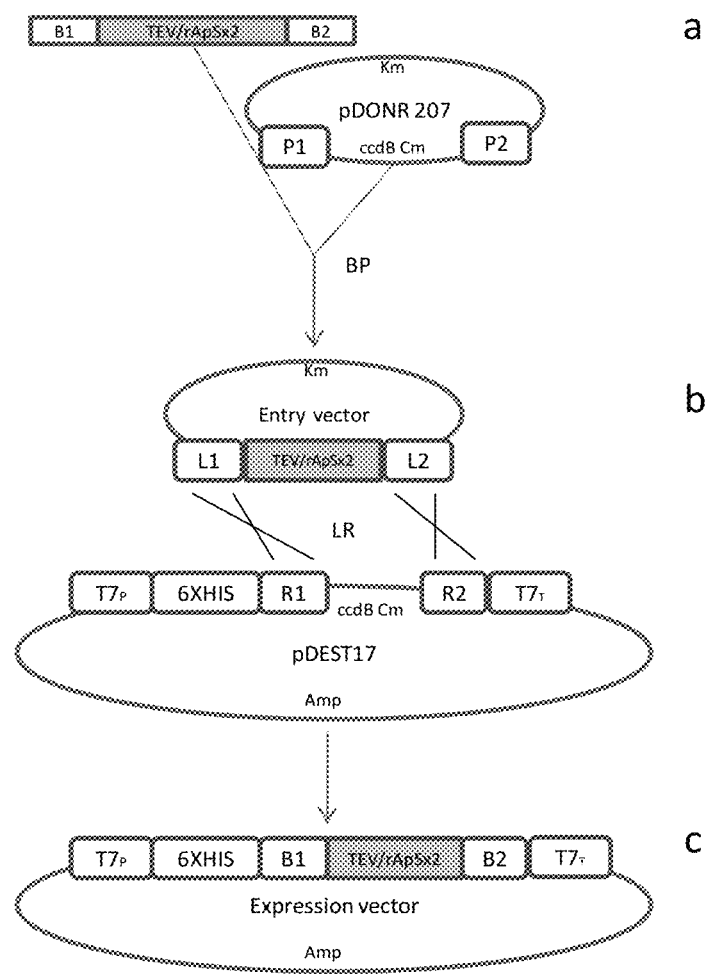
FIG. 1: Method of cloning in a suitable vector for the expression of the peptide in *E. coli*. a, BP reaction between TEV/rAp-Sx2 flanked in the ends by attB and pDONR 207. b, LR reaction between entry vector (obtained from BP reaction) and pDEST17. c, expression vector obtained from LR reaction.

Design of the Synthetic Gene: The Ap-S cDNA was designed using the reverse-translation of the sequence of 31 amino acids (MPVGIVIAPKKSPFTAKKPGPVLSGVK-AGPG) (SEQ ID No. 9) previously described based on *Argopecten purpuratus* hemocytes. Using GCUA software (Fuhrmann et al., 2004) and codons from *E. coli* and *N. tabacum*, a synthetic gene for rAp-S (SEQ ID No. 1) was obtained. A recognition site for the TEV-protease in the 5' end was added. Two full oligonucleotide sequences, TEV/rAp-S and TEV/rAp-Sx2 [TEV/rAp-S::TEV/rAp-S] were synthetized at Integrated DNA Technologies, Inc. (Iowa, U.S.A.) and cloned into a pSMART vector (Lucigen, Middletown, Wis.), generating the vectors pSMART-TEV/rAp-S and pSMART-TEV/rAp-Sx2 (FIG. 1).

Example 2

Generation of the Donor-gene Vector for Expression in *E. coli*: Using pSMART-TEV/rAp-S and pSMART-TEV/rAp-Sx2 as templates, additional attB recombination sequences were flanked at TEV/rAp-S and TEV/rAp-Sx2 ends using a double PCR amplification strategy. In the first step (pre-amplification), adapter-primers adpF (SEQ ID No. 2) and apdR (SEQ ID No. 3) were used to amplify a fragment of 147 bps [adpF::TEV/rAp-S::adpR] and 261 bps [adpF::TEV/rAp-Sx2::adpR]. The PCR reaction was performed in a total volume of 50 µL containing 5 µL of Accuprime Pfx reaction mix 10 times. (Invitrogen, Carlsbad, Calif.), 1 µL of each primer (10 mM), 0.5 µL AccuPrime Pfx DNA polymerase (2.5 U/µL; Invitrogen), 0.5 µL of pSMART-TEV/rAp-S (1:100 diluted) and pSMART-TEV/rAp-Sx2 (1:100 diluted) and 42 µL of H2O for each reaction. The thermal profile was a starting denaturation step at 95° C. for 2 min followed by 10 cycles of 94° C. for 15 s, 55° C. for 30 s and 68° C. for 135 s. A second round of PCR was performed on 10 µL of the pre-amplified product using the primers attB1 (SEQ ID No. 4) and attB2 (SEQ ID No. 5) resulting in the synthesis of a 181 bps fragment (SEQ ID No. 6) [attB1::TEV/rAp-S::attB2] (FIG. 2a) and 295 bps fragment (SEQ ID No.12) [attB1::TEV/rAp-Sx2::attB2] (FIG. 1a). The PCR reaction was performed in a total volume of 50 µL, containing 5 µL Accuprime Pfx reaction mix 10× (Invitrogen), 4 µL of each primer (10 µM), 0.5 µL AccuPrime Pfx DNA polymerase (2.5 U/L; Invitrogen), and 26.5 µL of H2O. The applied thermal profile had a starting denaturation at 95° C. for 1 min followed by 5 cycles of 94° C. for 15 s, 45° C. for 30 s and 68° C. for 125 s, the final round of amplification consisting of 20 cycles of 94° C. for 15 s, 55° C. for 30 s and 68° C. for 135 s. The amplification products were electrophoretically resolved in a 1% agarose gel and stained with ethidium bromide. The amplified 181 bps and 295 bps products were excised and purified using QiaexII Gel Extraction Kit (Qiagen, Germany) following the protocol described by the manufacturer. The obtained DNA was used for a "BP recombination" reaction with the entry vector pDONR207 (Invitrogen, U.S.A.). The BP Clonase Enzyme Mix (Invitrogen) was used for the reaction according to the manufacturer's protocol. The resulting entry vectors (pDNOR207-TEV/rAp-S and pDNOR207-TEV/rAp-Sx2) (FIGS. 1b y 2b) were used for the transformation of chemically competent *E. coli* DHS.alpha. using standard procedures, and the recombinant clones were grown overnight in LB-agar plates supplemented with 25 mg/L of gentamicin. Positive clones were confirmed by sequencing; by BsrGI enzyme restriction analysis resolved in agarose gel, and with specific PCR reactions.

Figure 2:
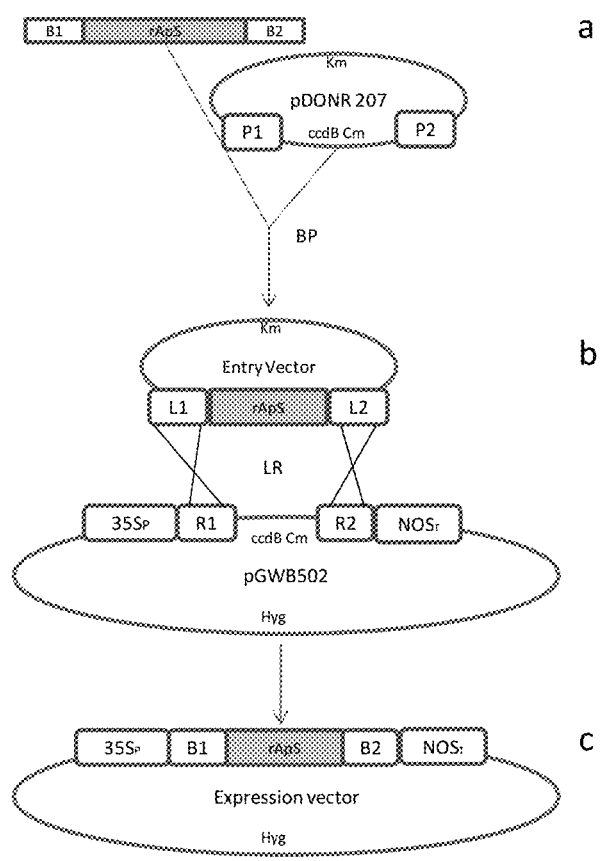
FIG. 2: Method of cloning in a suitable vector for the expression of the peptide in plants or plant cells transformed using *A. tumefaciens* as an agent. a, BP reaction between TEV/rAp-S flanked in the ends by attB and pDONR 207. b, LR reaction µbetween entry vector (obtained from BP reaction) and pGWB502. c, expression vector obtained from LR reaction.
Figure 3:
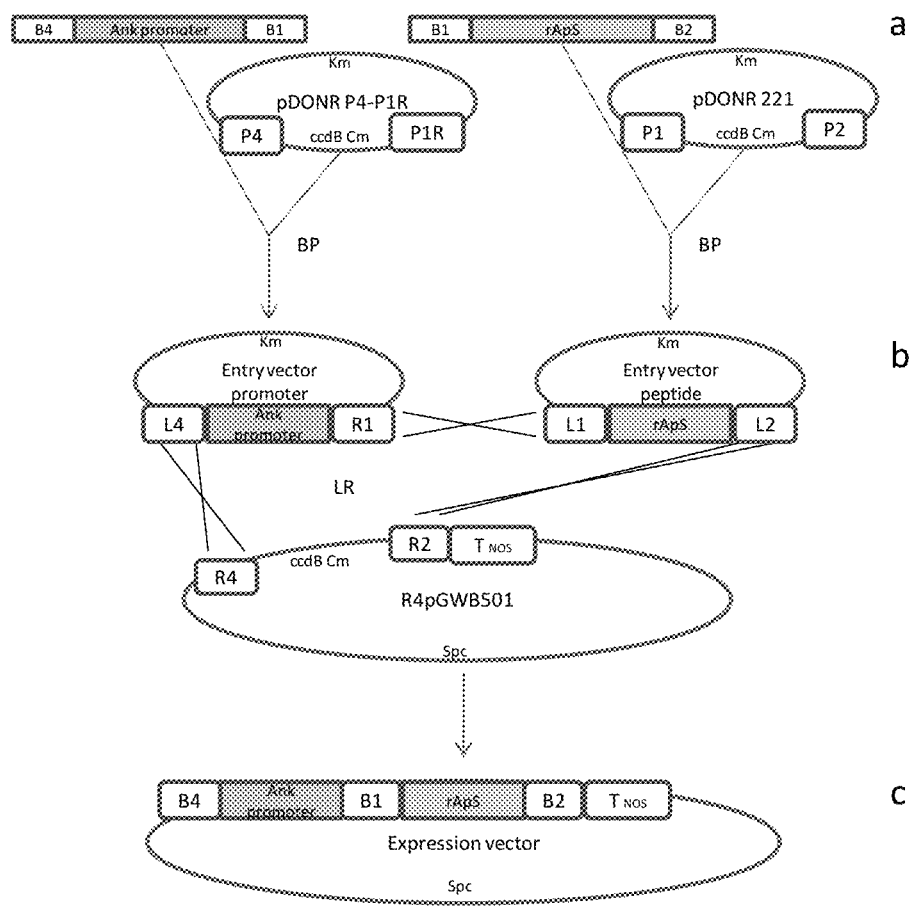
FIG. 3: Method of cloning in a suitable vector for the expression of the peptide in a plant with *A. tumefaciens* as a vector. a, two parallel BP reaction, first, between Ank promoter flanked in the ends by attB and pDONR P4-P1R and second, TEV/rAp-S flanked in the ends by attB and pDONR 221. b, LR reaction between entry vectors (obtained from BP reactions) and R4pGWB501 multisite vector. c, expression vector obtained from LR reaction.

A Gateway™ LR recombination reaction was performed between pDNOR207-TEV/rAp-Sx2 and pDEST17 (Invitrogen, U.S.A.) (FIG. 2c). For the reaction, LR Clonase Enzyme Mix (Invitrogen, U.S.A.), PstI-linearized pDNOR207-TEVrAp-Sx2 and pDEST17 vector were incubated according to the manufacturer's procedures. Then, 5 µL of the recombinant mixture was used for direct transformation of chemically competent *E. coli* BL21 (DE3) following standard procedures (Sambrook et al., 1989) and the transformed *E. coli* were grown overnight in LB-agar plates supplemented with carbenicillin 100 mg/L. Primary positive clones were screened by PCR, and the final selected clone containing the pDEST17-pre-TEVrAp-Sx2 expression vector was confirmed by sequencing.

Example 3

Expression and purification of AMP in *E. coli* BL21 (DE3): A strain of *E. coli* BL21 was inoculated into 5 mL of LB medium containing 100 mg/L carbenicillin and grown overnight at 37° C. under agitation at 180 rpm. Then the 5 mL were used as inoculum for 100 mL of LB medium and grown for 3 h, with the same concentration of antibiotic and growth described conditions. After this period, the culture medium was supplemented with isopropyl-b-D-thio-galactopyranoside (IPTG) 1 mM for induction of protein. Cultivation was continued for 3 more hours and finally centrifuged at 5000 rpm for 10 min to form a pellet of bacteria and the supernatant was carefully removed. The pellet was mixed by vortexing and pipetting the solution B-PER (Thermo Scientific) in a ratio of 4 mL of B-PER per gram of pellet, adding 2 µL of Lysozyme (Thermo Scientific) and 2 mL of DNase I (Thermo Scientific) per mL of B-pER used. The mixture was incubated under constant stirring for 15 min. Then the lysate was centrifuged at 15,000×g for 5 min to separate the soluble fraction from the insoluble which was removed carefully with pipette. The insoluble fraction was again suspended in the solution Solubilization Inclusion Body Reagent (Thermo Scientific) at a ratio of 8 mL of solution per g of insoluble pellet. The mixture was homogenized under constant agitation for 30 min at room temperature. Once homogenized, it was centrifuged at 27,000×g for 15 min and the supernatant containing the re-solubilized fraction is collected. Then proteolysis of 100 µg of recombinant protein with protease ProTEV Plus (Promega) was performed at 30° C. overnight under manufacturer's instructions. Fractions of peptides released from proteolysis are re-naturalized with a dialysis cassette Slide-A-Lyzer Dialysis Cassette G2 2.0 MWCO (Thermo Scientific) and protease inhibitor decreasing the concentration of 6M UREA with Tris 25 mM, pH=5.0 each 8 h during 5 d to final 25 mM Tris solution, 150 mM NaCl pH=5.0. Finally, the peptides released by proteolysis and re-naturalized are passed through the 0.5 mL Pierce Concentrator 10K MWCO PES column (Thermo Scientific) where the eluate from the column contain the peptides discarding E. coli proteins. The visual confirmation was made with TTS gel for the resolution of peptides (Schägger, 2006).

Example 4

Mass Spectrometry Analysis of Purified pre-TEV/rAp-S and rAp-S: Re-purified samples of the peptides were automatically analyzed in an ABi4800 MALDI TOF/TOF mass spectrometer (Applied Biosystems, Framingham, Mass., USA) under positive ion reflector mode (ion acceleration voltage of 25 kV for MS acquisition and 1 kV for MSMS) or linear mode for peptides ≥4 kDa. The resulting spectra were stored in the ABi4000 Series Explorer Spot Set Manager. The MS and MSMS fragment ion spectra were smoothed and corrected to zero-baseline using routines embedded in the ABi4000 Series Explorer Software v3.6. External calibration was used to reach a typical mass measurement accuracy of <25 ppm.

Example 5

Recombinant Peptide Expression in *Nicotiana tabacum*:
a) Construction of input vector with pDONRP4-P1 R and pDONR221. The ankyrin promoter sequence was amplified with the primers attB4 (5'-GGGGACAACTTTGTATA-GAAAAGTTGTC-NNN-3') (SEQ ID No. 7) and attB1r (5'-GGGGACTGCTTTTTTGTACAAACTTGC-NNN-3') (SEQ ID No. 8), and the rAp-S sequence was amplified with attB1 (5'-NNN3 GGGGACAAGTTTGTA-CAAAAAAGCAGGCTTC-3') (SEQ ID No. 10) and attB2 (5'-GGGGACCACTTTGTACAAGAAAGCTGGGTC-NNN-3') (SEQ ID No. 11), where NNN represents the specific nucleotide sequence. The following PCR conditions were used: 5 µL of Reaction Mix 10× AccuPrime Pfx (Invitrogen), 4 µL of each primer (10 mM each), 0.5 µL of AccuPrime Pfx DNA Polymerase (2.5 U/µL; Invitrogen), 0.5 µL of vine genomic DNA and 36 µL of ddH$_2$O. The thermal profile was initial denaturation at 95° C. for 2 min, followed by 29 cycles with denaturation at 94° C. for 15 sec, annealing at 55° C. for 30 sec and extension at 68° C. for 2 min 15 sec. The results of the amplifications were visualized by electrophoresis on a 1% agarose gel with ethidium bromide staining (Sambrook et al., 1989). The bands corresponding to the expected size were cut and purified with QiaexII Gel Extraction Kit (Qiagen, Germany) according to the manufacturer's instructions. The purified fragments of this reaction were used for recombination with the pDONRP4-P1 R and pDONR221 vectors (Invitrogen) with "BP Clonase" (Invitrogen) following the manufacturer's instructions. The vectors were cloned in E. coli DH5a grown in LB medium supplemented with 50 mg/L kanamycin.

b) Construction of expression vector with R4pGWB401. For the construction of the plant expression vector, the vectors pDONRP4-P1R-Ankyrin and pDONR221-rAp-S containing the regulatory and coding sequences, respectively, were recombined with vector R4pGWB401 (Nakagawa et al., 2009) using "LR Clonase" (Invitrogen). The resulting vector was cloned in E. coli DH5a grown in LB medium supplemented with 50 mg/L spectinomycin.

c) Construction of expression vector with pGWB502. For the construction of the plant expression vector, the pDONR207-TEV/rAp-S vector containing the chimeric gene and the target vector pGWB502 (Nakagawa et al., 2007) were recombined using "LR Clonase" (Invitrogen). The resulting vector was cloned in E. coli DH5a and grown in LB medium supplemented with 50 mg/L spectinomycin.

d) Transformation of tobacco: For obtaining genetically modified tobacco plants with the expression vector, the protocol of Sparkes et al. (2006) was used. Young leaves of approximately 4-6 weeks were infiltrated with a solution containing acetosyringone 1M, sodium orthophosphate dodeca-hydrate (Na$_3$PO$_4$.12H$_2$O) 2 mM, IVIES (2-[N-morpholin]-ethanesulfonic acid; Phytotechnology Labs) 50 mM, D-glucose 25 mM and *A. tumefaciens* 3101 (OD.sub.600=0.3) harboring the vector to evaluate the plant material. After 72 hours of infiltration, the leaves of the plant were removed, sterilized with a 10% solution of sodium hypochlorite, washed with sterile ddH.sub.20 and cut into square pieces of approximately 1 cm$^2$. The fragments were cultured in Petri dishes containing 4.43 g/L germination medium (MS-S) of Murashige and Skoog (1962), supplemented with vitamins (Phytotechnology Labs, USA), 0.8% (w/v) agar TC (Phytotechnology Labs), 3.0% (w/v) sucrose (Phytotechnology Labs), 0.1 mg/L indole butyric acid (IBA, Sigma Aldrich, USA), 0.8 mg/L 6-benzylaminopurine (BAP; Sigma Aldrich), 200 mg/L carbenicillin (Sigma Aldrich), 200 mg/L timentin (Phytotechnology Labs) and 300 mg/L kanamycin (Phytotechnology Labs). The explants were maintained in MS-S to sprout, which occurred in approximately 3 weeks. Subsequently, the shoots were excised and cultured for two weeks in Petri dishes with 4.43 g/L rooting medium (MS-R) of Murashige and Skoog supplemented with vitamins, 0.8% (w/v) TC agar, 3.0% (w/v) sucrose, 0.5 mg/L indole butyric acid (IBA), 200 mg/L carbenicillin, 200 mg/L timentin and 300 mg/L kanamycin. Finally, regenerated plantlets were planted separately in flasks (150 mL) containing base MS medium (4.43 g/L of Murashige and Skoog supplemented with vitamins, 0.8% [w/v] national agar (Veronica Sepulveda, Chile) and 3.0% [w/v] sucrose). The plants were maintained in this medium until evaluation.

Example 6

Functionality Tests of Peptides Produced in Bacteria and Plants:

a) Evaluation of Peptides obtained in *E coli*: Isolates from *Botrytis cinerea, Fusarium oxysporum, Trichoderma harzianum* and *Alternaria* spp. were treated with the purified fractions of the digested and non-digested peptides (pre-TEV/rAp-S and rAp-S) derived from the selected recombinant clone of *E. coli* (Example 3).

The potential antifungal abilities of both peptides were evaluated by analysis of the growth patterns of these fungi on agar PDA (potato-dextrose) in Petri dishes supplemented with protein extracts at 500 µg/L (162 nM) and 250 µg/L (81 nM), respectively.

The control growth assays were performed on PDA dishes without peptides. The growth patterns were evaluated according the amount of time required for the fungi to reach the dish walls in the control plates (10 days after inoculation in darkness at room temperature). Structural images of the fungi hyphae patterns were obtained using a Olympus® microscope (Center Valley, Pa., USA), and spores were counted using a Neubauer camcorder (Brand®, Wertheim, Germany) at 40×. The data were subjected to analyses of variance, and averages were separated by the least significant difference test (LSD) at the 5% level of significance using Statgraphics Centurion XV (Manµistics Inc., Rockville, Md., USA). Petri dishes containing grown fungi were scanned and digitalized for statistical processing. The area of the mycelia was quantified using Gel-Pro Analyzer 4.0 (Media Cybernetics, Minneapolis, Minn., USA), and surface values in pixels were transferred to Excel (Microsoft Corporation, USA) for analysis. The average value of the colored haloes was calculated using scanned images of five repetitions on the tenth day after inoculation. The collected data were subjected to variance analysis, and the averages separated by LSD at the 5% level of significance. The confrontation results of the peptides are shown in tables 1 and 2. Table 1 shows the spore count. Table 2 shows the quantification of the area of the mycelium in pixels.

Example 7

Figure 4:
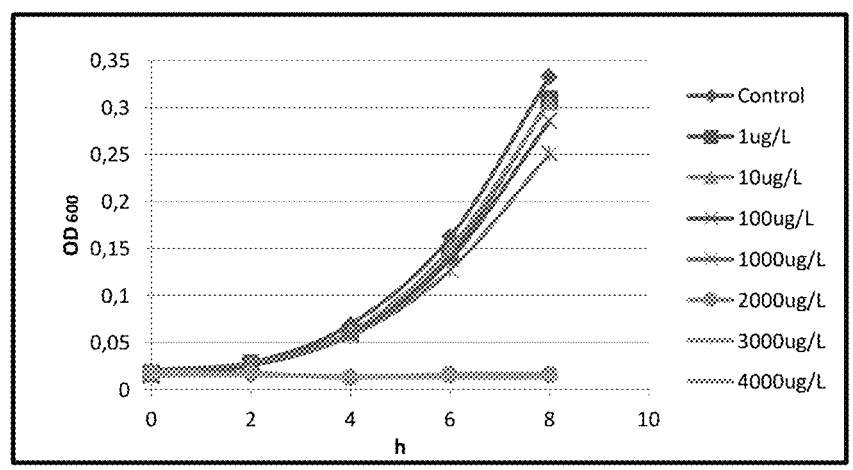
FIG. 4: Growth inhibition assays of *Xanthomona campestris* (G−) at different peptide concentrations. The maximum inhibition was reached between 2,000 and 4,000 µg/L.
Figure 5:
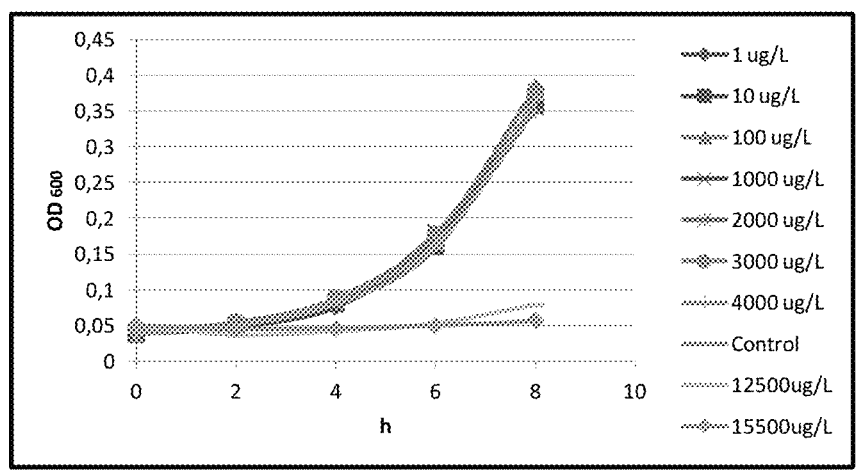
FIG. 5: Growth inhibition assays of *Clavibacter michiganensis* (G+) at various peptide concentrations. The maximum inhibition was reached between 12,500 and 15,500 µg/L.
Figure 6:
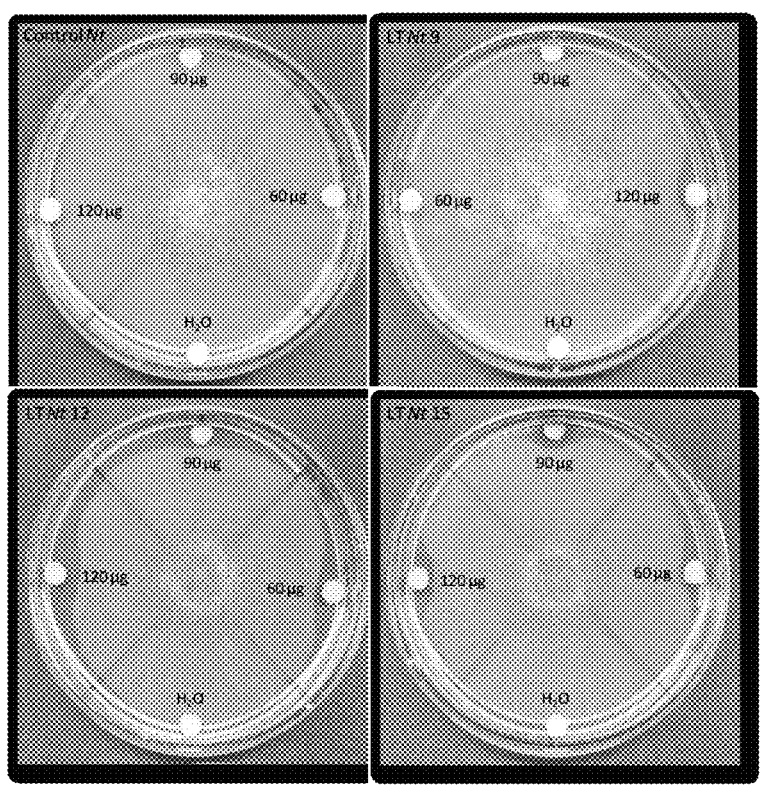
FIG. 6: Assay of the total protein extract from four lines of transgenic *Nicotiana tabacum*. The plates show growth inhibition halos on a lawn of *T. harzianum*.

Growth Inhibition Assays at Different Concentrations of Peptide rAp-S: The inoculation of 5 mL of LB was performed with 100 µL of bacteria (*Xanthomona campestris* and *Clavibacter michiganensis*), followed by overnight culturing. The absorbance was quantified at $OD_{600}$. Once the Abs was quantified, dilutions were made to obtain an Abs to inoculate each tube with the same concentration of bacteria with an initial $OD_{600}$ of 0.04. Different peptide concentrations were used. Each tube was inoculated with an rAp-S peptide concentration, as shown in Tables 3 and 4. A final volume of 10 mL in a 50 mL tube was used. In addition, a control without peptide was used for each bacterium. The kinetics of the process was followed for 8 h from time zero, determining the Abs every 2 h. The sample was 1 mL, as shown in FIGS. 4 and 5. The data were logarithmically transformed for the exponential phase of kinetics, and a linear regression was performed on the transformed data. The slope of the regression is the specific growth rate of the bacteria: $\mu$ ($h^{-1}$). The p (specific growth rate) was compared by LSD, and the data were interpreted, as shown in Tables 3 and 4.

TABLE 3

Specific growth rate for *Xanthomona campestris*, and its comparison to LSD

| | Xanthomona campestris | | |
|---|---|---|---|
| Tube | $\mu(h^{-1})$ | SD | LSD |
| Control | 0.385 | 0.011 | a |
| 1 µg/L | 0.371 | 0.011 | a |
| 10 µg/L | 0.375 | 0.012 | a |
| 100 µg/L | 0.386 | 0.007 | a |
| 1 mg/L | 0.329 | 0.014 | b |
| 2 mg/L | 0.015 | 0.002 | c |
| 3 mg/L | −0.012 | 0.002 | c |
| 4 mg/L | −0.019 | 0.002 | c |

TABLE 1

The spore count

| | Spore count | | | | | | | | | | | |
|---|---|---|---|---|---|---|---|---|---|---|---|---|
| Purified peptide fraction | *Trichaderma harzlanum* | | | *Botrytis cinerea* | | | *Alternaria* sp | | | *Fusarium oxysporum* | | |
| | Average | SD | LSD | Average | SD | LSD | Average | SD | LSD | Average | SD | LSD |
| rAp-S | $5.0 \times 10^6$ | $1.0 \times 10^5$ | a | $1.02 \times 10^6$ | $2.31 \times 10^5$ | a | 0 | 0 | a | $7.6 \times 10^5$ | $8.98 \times 10^4$ | a |
| Pre-TEV/rAp-S | $1.40 \times 10^7$ | $1.55 \times 10^6$ | b | $5.98 \times 10^5$ | $8.92 \times 10^4$ | a | $1.82 \times 10^6$ | $2.33 \times 10^5$ | b | $1.17 \times 10^6$ | $7.27 \times 10^4$ | b |
| Control | $2.14 \times 10^7$ | $1.57 \times 10^6$ | c | $9.17 \times 10^6$ | $4.93 \times 10^5$ | b | $3.15 \times 10^6$ | $9.29 \times 10^4$ | c | $1.76 \times 10^6$ | $1.31 \times 10^{5'}$ | c |

TABLE 2

Quantification of the area of the mycelium in pixels

| | Central area (pixeles) | | | | | | | | | | | |
|---|---|---|---|---|---|---|---|---|---|---|---|---|
| Petri dish/agar | *Trichoderma harzianum* | | | *Botrytis cinerea* | | | *Alternaria* sp | | | *Fusarium oxysporum* | | |
| PDA plus: | Average | SD | LSD | Average | SD | LSD | Average | SD | LSD | Average | SD | LSD |
| rAp-S | 85718 | 12155 | a | 170781 | 69412 | a | 412403 | 14385 | a | 511699 | 55046 | a |
| Pre-TEV/rAp-S | 623533 | 95785 | b | 235089 | 24328 | a | 430672 | 7665 | a | 498691 | 78927 | a |
| Control | 820412 | 42611 | c | 824804 | 53429 | b | 460848 | 18115 | b | 670810 | 98093 | b |

TABLE 4

Specific growth rate for *Clavibacter michiganensis*, and its comparison to LSD

| | *Clavibacter michiganensis* | | |
|---|---|---|---|
| Tube | μ (h$^{-1}$) | SD | LSD |
| Control | 0.072 | 0.011 | a |
| 1 μg/L | 0.070 | 0.008 | a |
| 10 μg/L | 0.069 | 0.010 | a |
| 100 μg/L | 0.075 | 0.010 | a |
| 1 mg/L | 0.069 | 0.006 | a |
| 2 mg/L | 0.069 | 0.009 | a |
| 3 mg/L | 0.073 | 0.009 | a |
| 4 mg/L | 0.066 | 0.009 | a |
| 12.5 mg/L | 0.009 | 0.001 | b |
| 15.5 mg/L | 0.003 | 0.0003 | b | b) Evaluation of the rAp-S Produced in *Nicotiana tabacum*

For the evaluation of the rAp-S produced in *Nicotiana tabacum*, total protein was extracted from 14 transgenic lines, and 30 μg of total protein from each plant was spread on a Petri plate containing PDA. Each plate was inoculated with a suspension of 2×10$^9$ spores of *T. harzianum* as the growth inhibition indicator. After 7 d, the growth inhibition was determined visually, and no biological or statistical analysis was performed if there was any plaque inhibition. The three top lines that generated some degree of growth inhibition were selected, and a further test was performed with 60, 90 and 120 μg of total protein in the same plate. The plate was divided into four equal areas, and in each area, a Whatman paper disk was placed on the edge with the required peptide amount or a water control. All peptide amounts (60, 90 and 120 μg) were added to a volume of 100 μL to ensure that the experiment was more homogeneous. Each plate was inoculated with a spore suspension of $2\times10^9$ of *T. harzianum* in the center. After 3 days, the inhibition area was determined with the program Pro Analyzer Gel using the disk peptide areas where the fungus did not grow (FIG. 6). The areas of inhibition, in pixels, of the transgenic lines (TL) of *Nicotiana tabacum* (Nt) were determined: TL Nt 9, TL Nt 12, TL Nt 15 and Control Nt (untransformed). Each line, including the Control Nt, was analyzed separately. In the LSD analysis, the different amounts of total protein (60, 90, and 120 μg and water) were compared. The Control Nt and water controls for each TL Nt showed no inhibition of *T. harzianum* (Table 5).

Inhibition of *T. harzianum* with total protein Extracts from Transgenic lines (LT) of *Nicotiania tabacum* (NT) at increasing amounts (60, 90 and 120 μg) and a water control. The control Nt was a non transgenic plant. *No inhibition; **No statistical analysis These experimental examples were exemplifying and not limiting. Although the yields obtained and the activity of the recombinant peptide were successful in their objective of producing rAp-S active against economically relevant pathogens using bacteria and plants as sources of expression, the present invention does not exclude the potential use of this chimeric gene to express the said AMP in additional expression systems, such as yeast. The use of a medium/large scale of such peptides is desirable for the control of plant pests.

Optionally and as a non-limiting method, the methodology to be used for the implementation of the total protein extract of *N. tabacum* can be performed together with a suitable carrier.

Protein extraction was performed with a basic extraction buffer consisting of 1M sodium chloride, 0.1M sodium acetate, 1% PVP, 10 mM β-mercaptoethanol, 0.25% v/v Triton X-100, and 20% glycerol. This total extract can be diluted to the required concentration in $ddH_2O$ (pH between 4 and 5) and sprayed onto the plants. The plants can also be treated using alternative means.

The extracts of total protein from *E. coli* were prepared from the method described in Example 3 and then diluted in $ddH_2O$ (pH between 4 and 5) to the concentration required for spraying.

These preparations are suitable for the direct application to crops, plants, plant parts, roots and/or soil that is healthy or infested with fungi and/or phytopathogenic bacteria.

After obtaining the protein extracts from both *E. coli* and *N. tabacum*, a lyophilization step can be incorporated, which gives stability to the extract and allows storage at room temperature. Additionally, this step will facilitate the commercialization of the product.

In short, if the extract is obtained by synthesis in *E. coli*, the process is scaled to high volume bioreactors, ball or disc grinder, continuous or cake centrifuge, extract stripper column and a final lyophilizer to process this volume.

In the case that the process selected for obtaining the extract uses *N. tabacum*, an extension of cropland that allows the required demand to be met, ball grinder, continuous or cake centrifuge and a lyophilizer able to process the final high volume should be considered.

TABLE 5

| Inhibition area of *Trichoderma harzianum*, in pixels | | | | | | | | | | | | |
|---|---|---|---|---|---|---|---|---|---|---|---|---|
| | Petri dish Inhibition area of *Trichoderma harzianum* (pixeles) | | | | | | | | | | | |
| PDA | Control Nt | | | LT Nt 9 | | | LT Nt 12 | | | LT Nt 15 | | |
| plus | Average | SD | LSD | Average | SD | LSD | Average | SD | LSD | Average | SD | LSD |
| water | * | * | ** | * | * | ** | * | * | ** | * | * | ** |
| 60 μg | * | * | ** | 221.67 | 0.47 | a | 3416.5 | 94.5 | a | 1048.67 | 26.4 | a |
| 90 μg | * | * | ** | 516 | 108 | b | 3340 | 37 | a | 1930.5 | 36.5 | b |
| 120 μg | * | * | ** | 605 | 169.41 | b | 4185.5 | 271.5 | b | 2741 | 20 | c |

Inhibition of *T. harzianum* with total protein Extracts from Transgenic lines (LT) of *Nicotiania tabacum* (NT) at increasing amounts (60, 90 and 120 μg) and a water control.
The control Nt was a non transgenic plant.
* No inhibition;
** No statistical analysis

Example 8

In the original method of producing TEV-rAp-S incubation periods between 16 h to 18 h were used at −80° C. in 8M urea buffer for the re-suspended pellet of E. coli BL21, collected from 100 mL of culture. After the incubation and thawing of the mixture, the sample was centrifuged at 23000×g for 15 min, the supernatant was collected and submitted to the process of purification through affinity columns with immobilized metals, a process that takes approximately 5 h including regeneration of the column according to the manufacturer instructions for the Kit (QIAexpress® Ni-NTA Fast Start, QIAGEN, USA). The new method for the production of TEV-rAP-Sx2, now does not require incubation at low temperatures, long times and neither the use of affinity chromatography columns. The new methodology is based on generating cell disruption with buffer B-PER (bacterial protein extraction reagent with enzymes; Thermos Fisher Scientific, Meridian, Rockford, USA), separating the soluble fraction from the insoluble by centrifugation, removing this fraction tube and finally re-suspend the insoluble fraction with the buffer Inclusion Boby Solubilization Reagent (Thermo Fisher Scientific). Subsequently, resuspension is centrifuged at 23,000×g during 15 min and the supernatant is collected in which there is an enriched protein fraction of TEV-rApS by 80% (Thermo Scientific Manual) in this case. The values obtained in each case regarding the production of TEV-rAp-S and TEV-rAp-Sx2 are presented in Table 6, associated with their time and yields. After this process, for better purification, TEV-rApSx2 protein is digested by the ProTEV (Promega, USA) protease obtaining the release of two peptides rAp-S. The obtained rAp-S peptides, according to its low molecular weights are separated from other proteins by exclusion columns for a molecular weight cutoff (MWCO) of 10 kDa (Thermos Fisher Scientific, Meridian, Rockford, USA), where the eluted from the column is the fraction containing the peptides, being separated from other proteins and protease. This process decreases the times from 24 to 2 h and increases the yield from 185 µg/mL to 2.448 mg/mL (2448.00 µg/mL) equivalent to an increase of 13 times.

TABLE 6

Different times and yields for each methodology, for purified proteins TEV-rAp-S and TEV-rAp-Sx2

| Purification Parameters | Original Method (TEV-rAp-S) | New Method (TEV-rAp-Sx2) |
|---|---|---|
| Time | 24 hrs | 2 hrs |
| Yield | 185 µg/mL | 2.448 mg/mL (2448.00 µg/mL) |

It can be observed from table 6, that the new method and protein TEV-rAp-Sx2 gives a yield up to 13 times more efficient that the one with TEV-rAp-S.

SEQUENCE LISTING OF THE CHIMERIC GENE
SEQ ID No. 1 of the Synthetic Gene rAp-S
5'-ATG AAA AAT CTT TAT TTT CAA GGT ATG CCT
GTT GGT ATT GTT ATT GCT 5 CCT AAA AAA TCT
CCT TTT ACA GCT AAA AAA CCT GGT CCT GTT
CTG TCT GGT GTT AAA GCT GGT CCT GGT TAA-3'

SEQ ID No. 2 ADPF:
5'-AAA AAG CAG GCT TCA TGG AAA ATC TTT ATT
TTC AAG GTA-3'

SEQ ID No. 3 ADPR:
5'-AGA AAG CTG GGT CTT AAC CAG GAC CAG CTT
TAA CAC CA-3'

SEQ ID No. 4 ATTB1:
5'-GGG GAC AAG TTT GTA CAA AAA AGC AGG CTT
CAT GGA AAA TCT TTA TTT TC-3'

SEQ ID No. 5 ATTB2:
5'-GGG GAC CAC TTT GTA CAC GAA AGC TGG GTC
TTA ACC AGG ACC AGC TTT AA-3'

SEQ ID No. 6:
5'-GGG GAC AAG TTT GTA CAA AAA AGC AGG CTT
CAT GGA AAA TCT TTA TTT TCA GGT TAT GCC TGT
TGG TAT TGT TAT TGC TCC TAA AAA ATC TCC TTT
TAC AGC TAA AAA ACC TGG TCC TGT TCT GTC TGG
TGT TAA AGC TGG TCC TGG TTA AGA CCC AGC TTT
CTT GTA CAA AGT GGT CCC C-3

SEQ ID No. 7:
GGGGACAACTTTGTATAGAAAAGTTGTCNN N

SEQ ID No. 8:
GGGGACTGCTTTTTTGTACAAACTTGCNNN

SEQ ID No. 9:
Met Pro Val Gly Ile Val Ile Ala Pro Lys Lys
1               5                   10

Ser Pro Phe Thr Ala Lys Lys Pro Gly Pro Val
            15                  20

Leu Ser Gly Val Lys Ala Gly Pro Gly
        25                  30

SEQ No. 12:
GGGGACAAGTTTGTACAAAAAAGCAGGCTTCATGGAAAATCTTTATTTTC

AAGGTATGCCTGTTGGTATTGTTATTGCTCCTAAAAAATCTCCTTTTACA

GCTAAAAAACCTGGTCCTGTTCTGTCTGGTGTTAAAGCTGGTCCTGGTGA

AAATCTTTATTTTCAAGGTATGCCTGTTGGTATTGTTATTGCTCCTAAAA

AATCTCCTTTTACAGCTAAAAAACCTGGTCCTGTTCTGTCTGGTGTTAAA

GCTGGTCCTGGTTAAGACCCAGCTTTCTTGTACAAAGTGGTCCCC

What is claimed is:

1. A method for obtaining an antimicrobial peptide with the amino acid sequence SEQ ID No. 9, the method comprising the following steps:
   (a) producing the TEV-rAp-Sx2 protein from the gene with SEQ ID No. 12 in *E. coli*, a plant, a plant cell or transformed plant material;
   (b) preparing a protein extract comprising the TEV-rAp-Sx2 protein from the *E. coli*, a plant, a plant cell or a transformed plant material of step (a);
   (c) treating the protein extract of step (b) with a protease; and
   (d) purifying the antimicrobial peptide with SEQ ID No. 9 in one step with a size exclusion chromatography column with a molecular weight cutoff (MWCO) of 10 kDa by collecting a pass-through eluate from the column, the pass-through eluate comprising peptides with a molecular weight less than 10 kDa, wherein the purification step is performed without ionic chromatography or high-performance liquid chromatography.

2. The method of claim 1, wherein step (d) comprises a protein extraction of inclusion bodies from recombinant *E. coli*.

3. The method of claim 1, wherein said method is a mass production and purification of said peptide in *E. coli*.

4. The method of claim 1, wherein the method is a method for mass production of the antimicrobial peptide, and wherein step (a) comprises producing the antimicrobial peptide in a plant, plant cell or transformed plant material.

5. The method of claim 4, wherein the method is a mass production method of the antimicrobial peptide in the *Nicotiana tabacum* plant, *Nicotiana tabacum* plant cells or *Nicotiana tabacum* transformed plant material.

* * * * *

UNITED STATES PATENT AND TRADEMARK OFFICE
CERTIFICATE OF CORRECTION

PATENT NO. : 10,597,430 B2
APPLICATION NO. : 15/164549
DATED : March 24, 2020
INVENTOR(S) : Rodriguez et al.

It is certified that error appears in the above-identified patent and that said Letters Patent is hereby corrected as shown below:

On the Title Page

Item (30), Under "Foreign Priority Data" delete "Mar. 4, 2013 (CL)......13/784,243" and insert --CL 593-2012  March 5, 2012--.

Signed and Sealed this
Twentieth Day of October, 2020

Andrei Iancu
*Director of the United States Patent and Trademark Office*

SEQUENCE LISTING

<160> NUMBER OF SEQ ID NOS: 12

<210> SEQ ID NO 1
<211> LENGTH: 120
<212> TYPE: DNA

```
<213> ORGANISM: Artificial Sequence
<220> FEATURE:
<223> OTHER INFORMATION: Synthetic sequence

<400> SEQUENCE: 1
atgaaaaatc tttatttca aggtatgcct gttggtattg ttattgctcc taaaaaatct        60
ccttttacag ctaaaaaacc tggtcctgtt ctgtctggtg ttaaagctgg tcctggttaa      120

<210> SEQ ID NO 2
<211> LENGTH: 39
<212> TYPE: DNA
<213> ORGANISM: Artificial Sequence
<220> FEATURE:
<223> OTHER INFORMATION: Synthetic primer

<400> SEQUENCE: 2
aaaaagcagg cttcatggaa aatctttatt ttcaaggta                              39

<210> SEQ ID NO 3
<211> LENGTH: 38
<212> TYPE: DNA
<213> ORGANISM: Artificial Sequence
<220> FEATURE:
<223> OTHER INFORMATION: Synthetic primer

<400> SEQUENCE: 3
agaaagctgg gtcttaacca ggaccagctt taacacca                               38

<210> SEQ ID NO 4
<211> LENGTH: 50
<212> TYPE: DNA
<213> ORGANISM: Artificial Sequence
<220> FEATURE:
<223> OTHER INFORMATION: Synthetic primer

<400> SEQUENCE: 4
ggggacaagt ttgtacaaaa aagcaggctt catggaaaat ctttattttc                  50

<210> SEQ ID NO 5
<211> LENGTH: 50
<212> TYPE: DNA
<213> ORGANISM: Artificial Sequence
<220> FEATURE:
<223> OTHER INFORMATION: Synthetic primer

<400> SEQUENCE: 5
ggggaccact ttgtacacga aagctgggtc ttaaccagga ccagctttaa                  50

<210> SEQ ID NO 6
<211> LENGTH: 181
<212> TYPE: DNA
<213> ORGANISM: Artificial Sequence
<220> FEATURE:
<223> OTHER INFORMATION: PCR amplification product

<400> SEQUENCE: 6
ggggacaagt ttgtacaaaa aagcaggctt catggaaaat ctttattttc aaggtatgcc       60
tgttggtatt gttattgctc ctaaaaaatc tccttttaca gctaaaaaac ctggtcctgt      120
tctgtctggt gttaaagctg gtcctggtta agacccagct ttcttgtaca aagtggtccc      180
c                                                                      181

<210> SEQ ID NO 7
<211> LENGTH: 28
```

```
<212> TYPE: DNA
<213> ORGANISM: Artificial Sequence
<220> FEATURE:
<223> OTHER INFORMATION: Synthtic primer

<400> SEQUENCE: 7
ggggacaact tgtatagaa aagttgtc                                          28

<210> SEQ ID NO 8
<211> LENGTH: 27
<212> TYPE: DNA
<213> ORGANISM: Artificial Sequence
<220> FEATURE:
<223> OTHER INFORMATION: Synthetic primer

<400> SEQUENCE: 8
ggggactgct tttttgtaca aacttgc                                          27

<210> SEQ ID NO 9
<211> LENGTH: 31
<212> TYPE: PRT
<213> ORGANISM: Argopecten purpuratus

<400> SEQUENCE: 9

Met Pro Val Gly Ile Val Ile Ala Pro Lys Lys Ser Pro Phe Thr Ala
 1               5                  10                  15

Lys Lys Pro Gly Pro Val Leu Ser Gly Val Lys Ala Gly Pro Gly
            20                  25                  30

<210> SEQ ID NO 10
<211> LENGTH: 31
<212> TYPE: DNA
<213> ORGANISM: Artificial Sequence
<220> FEATURE:
<223> OTHER INFORMATION: Synthetic primer

<400> SEQUENCE: 10
ggggacaagt ttgtacaaaa aagcaggctt c                                     31

<210> SEQ ID NO 11
<211> LENGTH: 30
<212> TYPE: DNA
<213> ORGANISM: Artificial Sequence
<220> FEATURE:
<223> OTHER INFORMATION: Synthetic primer

<400> SEQUENCE: 11
ggggaccact ttgtacaaga aagctgggtc                                       30

<210> SEQ ID NO 12
<211> LENGTH: 295
<212> TYPE: DNA
<213> ORGANISM: Artificial Sequence
<220> FEATURE:
<223> OTHER INFORMATION: PCR fragment

<400> SEQUENCE: 12
ggggacaagt ttgtacaaaa aagcaggctt catggaaaat ctttatttc aaggtatgcc       60 tgttggtatt gttattgctc ctaaaaaatc tccttttaca gctaaaaaac ctggtcctgt     120
tctgtctggt gttaaagctg gtcctggtga aaatctttat tttcaaggta tgcctgttgg    180
tattgttatt gctcctaaaa aatctccttt tacagctaaa aaacctggtc ctgttctgtc    240
tggtgttaaa gctggtcctg gttaagaccc agctttcttg tacaaagtgg tcccc         295
```